(12) United States Patent
Masjedi

(10) Patent No.: US 6,174,164 B1
(45) Date of Patent: Jan. 16, 2001

(54) FERROMAGNETIC TOOTH BRUSHING SYSTEM

(76) Inventor: Saeed Masjedi, Box 55-5152, Los Angeles, CA (US) 90055-0152

(*) Notice: Under 35 U.S.C. 154(b), the term of this patent shall be extended for 0 days.

(21) Appl. No.: 09/576,186

(22) Filed: May 23, 2000

Related U.S. Application Data

(60) Provisional application No. 60/142,453, filed on Jul. 6, 1999.

(51) Int. Cl.$^7$ ..................................................... A61G 17/02
(52) U.S. Cl. ............................................. 433/80; 433/215
(58) Field of Search ................................. 433/80, 88, 215

(56) References Cited

U.S. PATENT DOCUMENTS 3,840,992 * 10/1974 English .................................... 433/80
5,833,600 * 11/1998 Young .................................... 600/300

* cited by examiner

Primary Examiner—Nicholas D. Lucchesi
(74) Attorney, Agent, or Firm—Robert M. Sperry

(57) ABSTRACT

An improved tooth cleaning system comprising a pump, at least one container of fluid containing ferromagnetic particles having diameters of the order of 10 microns, a hollow generally U-shaped mouthpiece formed of abrasion-resistant material, such as stainless steel, containing four U-shaped electromagnetic plates spaced about the interior of the mouthpiece, a hose communicating the interior of the mouthpiece with the pump, a selector for controlling the input to the pump and connecting the output from the pump to discharge pipe, an ultrasonic generator for pulsing the output of the pump, and an electronic device for controlling the energization of the electromagnetic plates.

8 Claims, 2 Drawing Sheets

FERROMAGNETIC TOOTH BRUSHING SYSTEM

RELATED CASES

This invention is described in my copending Provisional Application Ser. No. 60/142,453, filed Jul. 6, 1999.

FIELD OF INVENTION

This invention relates to dental care and is particularly directed to an improved method of cleaning teeth using magnetic energy and a toothpaste containing ferromagnetic particles.

PRIOR ART

It is well known that dental hygiene is vital to the overall health of an individual. Unfortunately, most people do not practice good dental hygiene, either because they are unaware of the proper techniques or do not spend sufficient time to carry out the procedures properly. Also, most presently available tooth brushing devices do not provide thorough cleaning, especially between the teeth and they are not %100 effective and are difficult or confusing to use and they are long process and tiresome. Numerous tooth-cleaning devices have been provided heretofore, but none of them have overcome these problems. Thus, none of the prior art tooth cleaning devices have been entirely satisfactory.

BRIEF SUMMARY OF INVENTION AND OBJECTS OF INVENTION

These disadvantages of the prior art are overcome with the present invention and improved tooth cleaning devices are proposed which are thorough and efficient in cleaning teeth and which is inexpensive to produce and purchase and simple to use.

These advantages of the present invention are preferably attained by providing an improved tooth cleaning device comprising A hollow generally U-shaped mouthpiece formed of abrasion-resistant material, such as stainless steel, containing four U-shaped HTSCMC (High temperature super conductive magnet coil ) strip spaced about the interior of said mouthpiece in every 4 corner of the mouthpiece strip to shoot up and down the ferromagnetic particles by magnetic energy for blasting teeth to remove bacteria, (Ferromagnetic toothpaste is regular toothpaste with %20 iron particles the size of particles are 10 micron).

Also we need magnets to pull particles through the slots by enormous force for flossing (if we can achieve such enormous power).

Also this is important that particle be shot like screw ball so mouthpiece has to shake during operation.

The basic idea of this invention is if you pour steel dust on top of paper and shake magnet under the paper thus steel dust shake on top of the paper and slowly remove writings on top of paper.

Another component of this device is Electromagnetic antenna running along the interior of the mouthpiece one on the top and one in lower part of mouthpiece to deliver heat and Electromagnetic energy to the surface of the teeth, (energy for energizing the antenna would be generated by external magnetron).

Another component of this device is external magnetron this magnetron has many function 1) to fry and disintegrate and sterilize bacteria by heat, note flashing time must be very short and several time 2) to increase inside temperature of the mouthpiece for better physical and chemical reaction 3) to convert plaque by heat to tar then to lacquer then to paint and then to protective film so to convert bad thing to useful thing by means of heat 4) causing all 3 toothpastes which are all termochemical to react with each other and to react with the surface of the teeth by means of heat and radio frequency energy and electric energy another word the antenna which located in the mouthpiece cavities would deliver heat and electricity and radio wave to create termochemical and Electro chemical and photochemical reaction of the toothpastes.

Another component of this device is A suck in suck out pump which is powerful pump with extremely fast reveres action,this pump has many function 1) to deliver water and liquids to the mouthpiece 2) to remove waste liquid from mouthpiece to waste tank 3) to inject other chemical to the operating water 4) to sand blast the teeth with suck in suck out action of pump 5) also as iron is heavier than water and it may accumulate on corners so suck in suck out pump would help to spread heavy iron particles.

Actually suck in suck out pump is so good for the job of blasting, so we really do not need any longer magnetic tooth past and its complex implementations.

Also on the mouth piece fluid tunnel between the jaws must be well built to allow sufficient liquid to spread around every corner, Also another major component of this device is hose communicating the interior of said mouthpiece with said pump.

Another component is an external ultrasonic generator for helping to remove the bacteria and pulsing output of said pump, Also we need microprocessor for controlling the energization of said HTSCMC strips and pumps valve and magnetron and ultrasonic switches.

Another component is and external static electricity generator (because there is study that static Electricity can help to remove bacteria).

Also part of invention is termochemical coated flossing string so when human floss it leaves traces of termochemical coating between slots so when magnetron activate chemical react with tooth surface to destroy bacteria and leave protective film on teeth.

Accordingly, it is an object of the present invention to provide an improved tooth cleaning system, as you see regular brush do not remove %100 of bacteria because it can not reach microscopic canyon of the surface of the teeth but because we are using sand blasting technique we can reach every microscopic canyon of surface of the teeth, also regular tooth brush can not fry remaining %1 bacteria that are the cause of all the problems of cavities, and this remaining bacteira can not be remove by brushing or even sand blasting but this system because use magnetron for delivering heat and radio energy can fry remaining bacteria also regular brushing technique does not use multiple tooth past but because we are using muliple toothpaste and chemicals thus we can use extremely strong chemicals to complete the %100 task, also regular brushing does not apply protective film in the end of process, protective film can add 10 time more protection Another objection of the this invention is to attack bacteria not only with one system but with many system at once.

Another object of the present invention is to provide an improved tooth cleaning system which is thorough and efficient.

Another objection is fast process of cleaning something like 15 second, because it cleans all teeth at once not one by one and use electronic robot and strong chemicals. Another objection is because this device can blast bacteria at microscopic level and it can fry remaining bacteria and it can put protective film in the end of process thus brushing interval could be extended up to week (only if protective film is made right and apply right ) so we do not need to brush for week.

Another major objection of this invention is that most of the dangerous teeth disease comes from gums diseases, you see brushing can not penetrate deep in the gums opening but because of this device horizontal blasting effect which can shoot iron particles deep in the gums opening and pulls them up while they are bringing back contaminants with them, so this device is super for gum diseases.

Another objection of this invention is to eliminate need for dentins with this device people never need to go to dentist because it is super cleaner.

An additional object of the present invention is to provide an improved tooth cleaning system which is simple and inexpensive to produce and use Another objection of this invention is to save toothpaste and use inexpensive tooth paste because this device uses multi toothpaste and elementary toothpaste and chemicals.

Another objection of the present invention is thus we can clean our teeth while we are driving or we are in bed so it eliminate need to have sink and running water.

Another objection of this invention is not only applying protective film but dye as well so teeth could be dyed in exotic colors.

These and other objects and features of the present invention will be apparent from the following detailed description, taken with reference to the figures of the accompanying drawing.

DETAILED DESCRIPTION OF THE INVENTION

Figure 1:
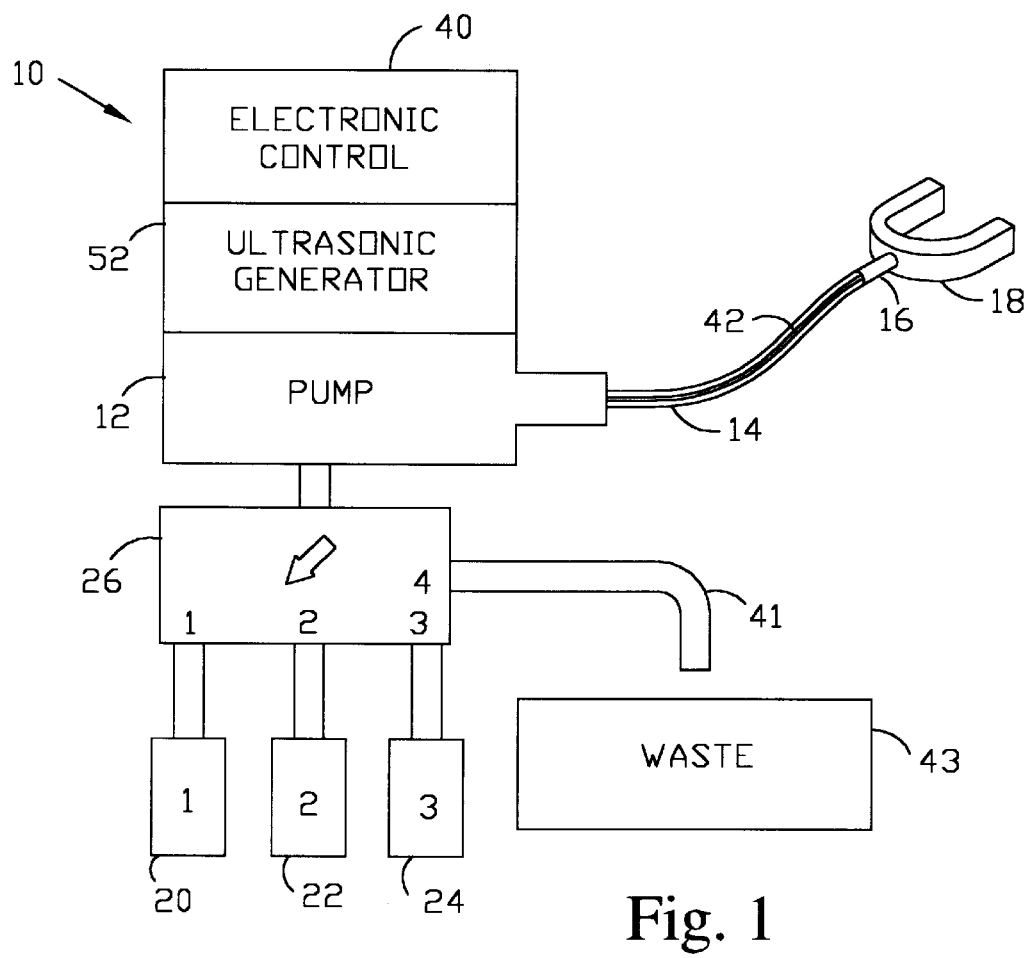
FIG. 1 is a diagrammatic representation showing a tooth cleaning system embodying the present invention.

In that form of the present invention chosen for purposes of illustration, FIG. 1 shows a tooth cleaning system, indicated generally at 10, having a pump 12 which is connected by hose 14 to supply fluid to and from the input fitting 16 of a hollow, generally U-shaped mouthpiece 18 formed of abrasion-resistant material, such as stainless steel or the like, having an inner wall 36 and an outer wall 38 which are spaced apart and joined by end pieces 37 to define and interior chamber 39. The pump 12 receives fluid from three containers 20, 22 and 24 for delivery to the mouthpiece 18 and exhausts fluids from the mouthpiece 18 through discharge pipe 41 into a suitable waste container 43, under the control of a suitable selector valve 26. The first container 20 holds a slurry formed of a strong alkaline liquid containing approximately 20% by weight of ferromagnetic particles, such as iron, having a diameter on the order of 10 microns.

Figure 2:
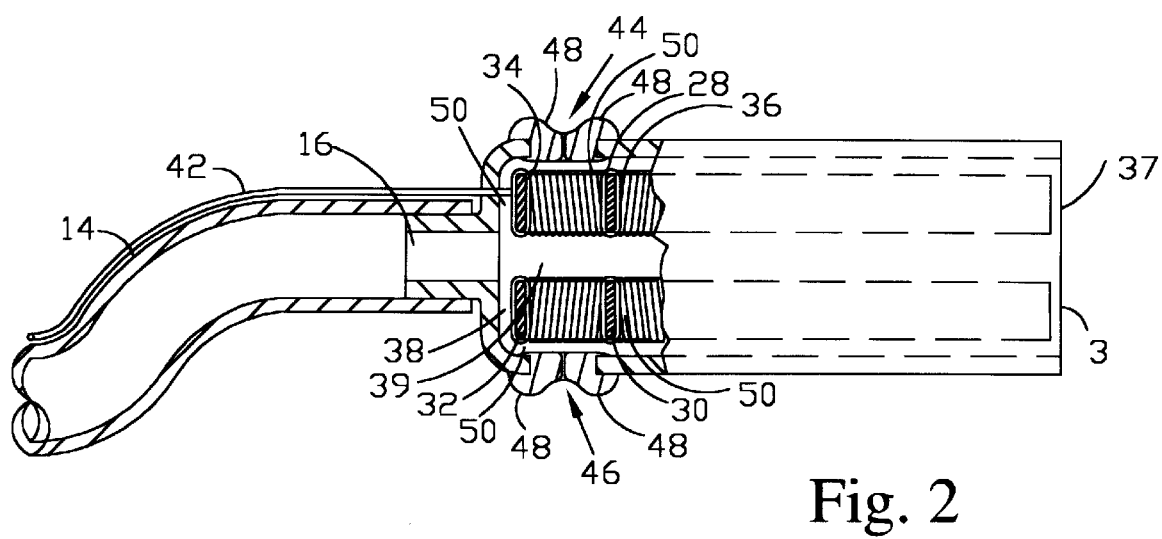
FIG. 2 is a side view, partly in section, of the mouthpiece of the tooth cleaning system of FIG. 1.
Figure 3:
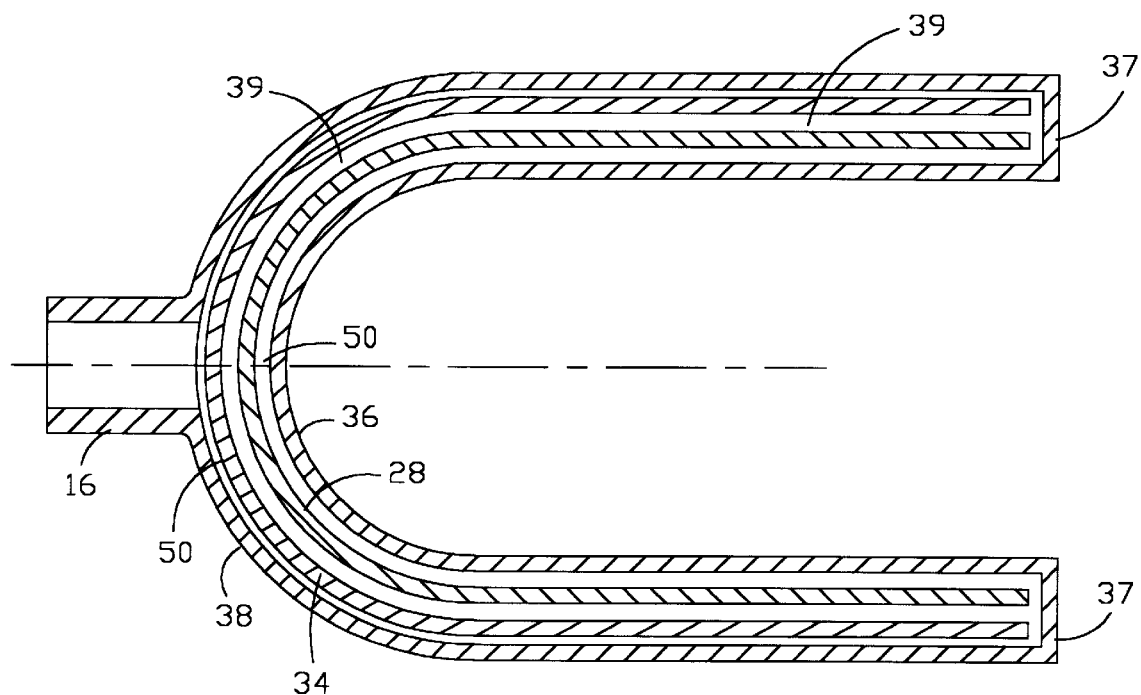
FIG. 3 Is a a transverse section through the mouthpiece of FIG. 1, taken on the line 3—3 of FIG. 2.
Figure 4:
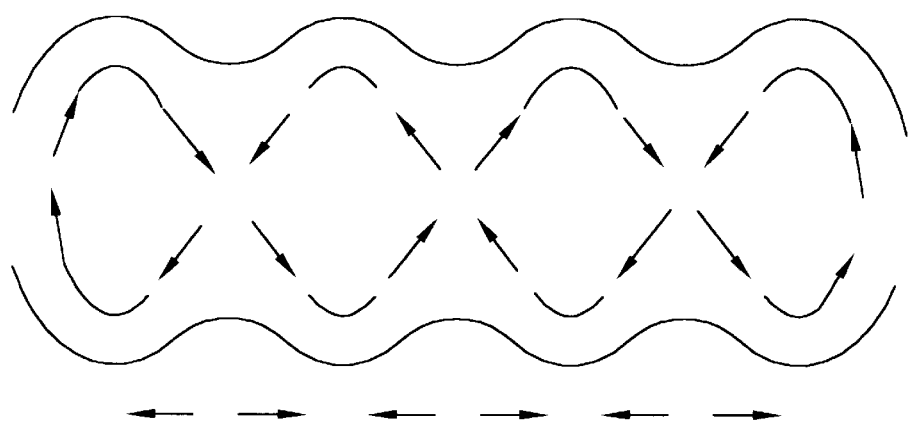
FIG. 4 is a diagrammatic representation showing the action caused by the pulsating fluid and the rotational activation of the electromagnetic plates of the tooth cleaning system of FIG. 1.

The second container 22 holds a liquid for neutralizing the alkalinity of the first liquid and the third container 24 holds a thermosensitive liquid which reacts with heat to form a protective film for the teeth. As best seen in FIGS. 2 and 3, the mouthpiece 18 is a hollow housing having four electromagnetic coils 28, 30, 32 and 34 which are generally U-shaped and are positioned in spaced relation about the interior of the mouthpiece 18. Thus, coil 28 is located adjacent the upper edge of the mouthpiece 18 adjacent the inner wall 36, while coil 30 is located adjacent the lower edge of the mouthpiece 18 adjacent the lower wall 36. Similarly, coil 32 is located adjacent the lower edge of the mouthpiece 18 adjacent the outer wall 38 and coil 34 is located adjacent the upper edge of the mouthpiece 18 adjacent the outer wall 38. An electronic controller 40 is located adjacent the pump 12 and is connected by wire 42 to actuate the coils 28, 30, 32 and 34 sequentially. As best seen in FIG. 2, the upper and lower surfaces of the mouthpiece 18 are open, as seen at 44 and 46, respectively, and are closed by strips 48 of gel-like plastic. When the user bites into the strips 48, the strips 48 allow the teeth to pass through, but tightly grip the gums to protect the gums against damage. Magnetrons antenna 50 are located between the electromagnetic coils 28, 30, 32 and 34 and the adjacent wall of the mouthpiece 18 and are actuated by the electronic controller 40 to deliver heat to the interior chamber 39 of the mouthpiece 18 to activate the tooth paste, destroy bacteria and disintigrate plaque. Finally, an ultrasonic generator 52 is mounted adjacent the pump 12 and serves to provide a pulsating motion to the fluid delivered by the pump 12 into the mouthpiece 18. electronic controller 40 can cause the pump 12 to provide strong pulsating action. This pulsating action, together with the sequential activation of the electromagnetic coils 28, 30, 32 and 34 acts upon the ferromagnetic particles in the fluid of the first container 20 to impart a spiral motion to the particles, as seen in FIG. 4, which significantly increases the cleaning action of the particles and serves to drive the particles through the crevices between the teeth for more complete cleaning.

In use, the user places the mouthpiece 18 in their mouth and bites down on it causing their teeth to penetrate through the gel-like strips 48 into the interior chamber 39 of the mouthpiece 18 and allowing the gel-like strips 48 to clamp against the gums. Then turns the device on Next, the microprocessor orders selector valve 26 to select the first container 20 and activates pump 12 to deliver the alkaline slurry from container 20 through hose 14 into chamber 39 of the mouthpiece 18. Then, microprocessor activates the ultrasonic generator 52 to cause pulsing of the slurry and turns on the electronic controller 40 to activate the electromagnetic coils 28, 30 32 and 34 to create the spiral motion of the ferromagnetic particles in the slurry. Also, during this period, the alkaline fluid of the slurry serves to chemically clean the teeth. After several seconds, microprocessor turns off the electronic controller and switches the selector valve 26 to discharge pipe 41 to allow pump 12 to exhaust the slurry from chamber 39 of the mouthpiece. When the slurry has been removed, microprocessor switches the selector valve 26 to container 22 to deliver the neutralizing fluid to chamber 39 of the mouthpiece. Now, the pulsation's caused by the ultrasonic generator 52 serve to move the fluid forwardly and rearwardly through the chamber 39 to thoroughly neutralize the alkalinity of the slurry from container 20. After several seconds, microprocessor again switches the selector valve to the discharge pipe 41 to remove the neutralizing fluid from chamber 39 of the mouthpiece 18. Next, microprocessor moves the selector valve 26 to container 24 to allow pump 12 to deliver the thermosensitive liquid from container 24 into chamber 39 of the mouthpiece 18 and turns on the electronic controller 40 to activate the magnetron antena 50 which heat the interior of chamber 39 and cause the thermosensitive liquid from container 24 to form a protective film on the teeth. Finally, microprocessor switches selector valve 26 to the discharge pipe 41 to remove the excess thermosensitive liquid and complete the cleaning process.

Obviously, numerous variations and modifications can be made without departing from the spirit of the present invention. Therefore, it should be clearly understood that the form of the present invention described above and shown in the figures of the accompanying drawing is illustrative only and is not intended to limit the scope of the present invention.

What is claimed is:

1. A tooth cleaning system comprising:

a pump, at least one container of fluid containing ferromagnetic particles having diameters of the order of 10 microns, a hollow generally U-shaped mouthpiece formed of abrasion-resistant material, four U-shaped electromagnetic coils spaced about the interior of said mouthpiece, a hose communicating the interior of said mouthpiece with said pump, selector means for controlling the input to said pump and connecting the output from said pump to a discharge pipe, and electronic means for controlling the energization of said electro-magnetic coils.

2. The system of claim 1 wherein:

said electromagnetic coils are energized sequentially.

3. The system of claim 1 wherein:

said fluid in said container is strongly alkaline.

4. The system of claim 1 further comprising:

a second container connected to said pump by said selector means and containing a fluid for neutralizing the alkalinity of the fluid in said one container.

5. The system of claim 1 further comprising:

an additional container connected to said pump by said selector means and containing a thermosensitive fluid, and means for creating heat within said mouthpiece to cause said fluid to form a protective film on the teeth of the user.

6. The system of claim 1 further comprising:

an ultrasonic generator connected to cause pulsation of the fluid delivered by said pump to said mouthpiece.

7. The system of claim 6 wherein:

said ultrasonic generator and said electronic means cooperate to cause spiral movement of said ferromagnetic particles within said mouth-piece.

8. The system of claim 1 wherein:

the upper and lower surfaces of said mouthpiece are open, and gel-like strips close said surfaces in a manner to permit the user's teeth to penetrate into the interior of said mouthpiece yet to protect the user's gums from injury during the cleaning process.

* * * * *